United States Patent [19]

Moore

[11] 4,059,590
[45] Nov. 22, 1977

[54] CERTAIN 4-HALO-5-ARYL-1,2,3-DITHIAZOLE COMPOUNDS AND THEIR PREPARATION

[75] Inventor: Joseph E. Moore, Richmond, Calif.

[73] Assignee: Chevron Research Company, San Francisco, Calif.

[21] Appl. No.: 698,383

[22] Filed: June 21, 1976

[51] Int. Cl.$^2$ ............................................. C07D 285/00
[52] U.S. Cl. .................................. 260/306.8 R; 71/90; 260/465 E; 424/270
[58] Field of Search .................. 260/306.8 A, 306.8 R

[56] References Cited

PUBLICATIONS

Wannagat et al., Chem. Abstracts, 52:7317d (1958).

Primary Examiner—Richard J. Gallagher
Attorney, Agent, or Firm—D. A. Newell; Raymond Owyang

[57] ABSTRACT 4-halo-5-aryl-1,2,3-dithiazole, useful as fungicides, ovicides, insecticides and herbicides, are prepared by reacting a N-aryl cyanothioformamide and a sulfur dihalide in the presence of a catalytic amount of a formamide compound or quaternary ammonium salt.

9 Claims, No Drawings

CERTAIN 4-HALO-5-ARYL-1,2,3-DITHIAZOLE COMPOUNDS AND THEIR PREPARATION

BACKGROUND OF THE INVENTION

Patterson et al., "Ring Index", 2nd Ed., page 11, disclose 3H-1,2,4-dithiazole, 1,2-dithiazolidine, 1,3,4,-dithiazole and 1,3,4,-dithiazolidine.

U.S. Pat. No. 3,419,573, issued to Weinstock on Dec. 31, 1968, discloses the preparation of 1,2,5-thiadiazoles by the reaction of sulfur chloride and a cyanoformimidate.

U.S. Pat. No. 3,763,176, issued to G. K. Kohn and M. S. Singer on Oct. 2, 1973, discloses the preparation of 3-halo-5-alkyl-delta$^2$-thiadiazolin-4-one by the reaction of a sulfur dihalide and a N-alkyl cyanoformamide.

DESCRIPTION OF THE INVENTION

The dithiazole compounds of the invention may be represented by the formula

wherein X is fluoro, chloro, bromo or iodo, and Ar is phenyl, naphthyl, phenyl or naphthyl substituted with 1 to 3 of the same or different substituents selected from hydroxy, fluoro, chloro, bromo, iodo, cyano, nitro, benzoyl, formyl, alkanoyl of 2 to 6 carbon atoms, alkyl of 1 to 6 carbon atoms, haloalkyl of 1 to 2 carbon atoms and 1 to 5 of the same or different halogens selected from fluoro, chloro, iodo, or bromo, alkoxy of 1 to 4 carbon atoms, phenoxy, phenoxy substituted with 1 to 2 of the same or different substituents selected from hydroxy, fluoro, chloro, bromo, iodo, trifluoromethyl, trichloromethyl, nitro, cyano or alkyl of 1 to 4 carbon atoms.

A preferred class of dithiazole compounds is that wherein X is chloro or bromo and Ar is phenyl, naphthyl, or phenyl substituted with 1 to 2 of the same or different substituents selected from fluoro, chloro, bromo, iodo, cyano, nitro, benzoyl, alkyl of 1 to 4 carbon atoms, trifluoromethyl, trichloromethyl, tribromomethyl, phenoxy or phenoxy substituted with 1 to 2 of the same or different substituents selected from fluoro, chloro, bromo, iodo, nitro, trifluoromethyl, trichloromethyl or alkyl of 1 to 4 carbon atoms.

Another preferred class of dithiazole compounds is that wherein Ar is phenyl, naphthyl, phenyl or naphthyl substituted with 1 to 2 of the same or different substituents selected from fluoro, chloro, bromo, iodo, trifluoromethyl, trichloromethyl, tribromomethyl, alkyl of 1 to 4 carbon atoms or nitro.

The most preferred class of dithiazole compounds is that wherein X is chloro or bromo and Ar is phenyl, naphthyl or phenyl substituted with 1 to 2 of the same or different substituents selected from fluoro, chloro, bromo, iodo or alkyl of 1 to 4 carbon atoms.

Representative dithiazole compounds of the invention include:
 4-bromo-5-phenylimino-1,2,3-dithiazole
 4-chloro-5-(4-hydroxyphenylimino)-1,2,3-dithiazole
 4-fluoro-5-(1-naphthylimino)-1,2,3-dithiazole
 4-chloro-5-(2-chloronaphth-1-ylimino)-1,2,3-dithiazole
 4-chloro-5-(2-nitronaphth-1-ylimino)-1,2,3-dithiazole
 4-bromo-5-(5-cyanonaphth-2-ylimino)-1,2,3-dithiazole
 4-chloro-5-(4-iodophenylimino)-1,2,3-dithiazole
 4-chloro-5-(4-chloromethylphenylimino)-1,2,3-dithiazole
 4-chloro-5-(4-phenoxyphenylimino)-1,2,3-dithiazole
 4-bromo-5-(3-trichloromethylphenylimino)-1,2,3-dithiazole
 4-bromo-5-(3-formylphenylimino)-1,2,3-dithiazole
 4-chloro-5-(4-acetylphenylimino)-1,2,3-dithiazole
 4-chloro-5-(4-acetoxyphenylimino)-1,2,3-dithiazole
 4-chloro-5-(3-methoxyphenylimino)-1,2,3-dithiazole
 4-chloro-5-(4-[4-chlorophenoxy]phenylimino)-1,2,3-dithiazole, and
 4-chloro-5-(3-[4-cyanophenoxy]phenylimino)-1,2,3-dithiazole.

The dithiazole compounds of the invention are prepared by reacting a sulfur dihalide and a N-aryl cyanothioformamide, as depicted by the following reaction:

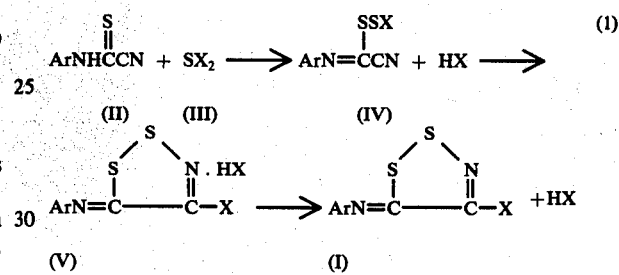

wherein Ar and X have the same significance as previously defined.

Reaction (1) is generally conducted by reacting substantially equimolar amounts of the sulfur dihalide and the cyanothioformamide, e.g., the molar ratios of sulfur dihalide (III) to cyanothioformamide (II) generally vary from about 1.5:1 to 1:1.5, although molar ratios from about 1.1:1 to 1:1.1 are preferred. Preferably, reaction (1) is conducted in the presence of catalytic amount of a formamide compound or a quaternary ammonium salt. Generally, amounts of formamide compound or quaternary ammonium salt per mol of sulfur dihalide vary from about 0.01 to 0.3, although amounts from 0.05 to 0.2 mols per mol of sulfur dihalide are preferred. Suitable formamide compounds include N,N-dialkylformamides and N-alkylformamides wherein the alkyl group(s) has from 1 to 4 carbon atoms, e.g., N-methylformamide, N,N-dimethylformamide or N,N-diethylformamide. Suitable quaternary ammonium salts are tetralkylammonium halides wherein the alkyl has 1 to 6 carbon atoms and the halide is fluoro, chloro, bromo or iodo, e.g., tetramethylammonium chloride or tetrabutylammonium bromide. When a quaternary salt is employed as a catalyst, the anion is preferable the same halide as the halide of the sulfur dihalide reactant.

In general, reaction (1) is accomplished by reacting the cyanothioformamide (IV), the sulfur dihalide (III) and the formamide or quaternary salt catalyst in an inert liquid organic diluent. Suitable inert diluents include alkanes and haloalkanes, such as hexane, isooctane, or dichloromethane; aromatic compounds, such as benzene, toluene, chlorobenzene; oxygenated hydrocarbon such as acyclic alkyl ethers, such as dimethoxyethane and dibutyl ether; and cyclic ethers such as dioxane, tetrahydrofuran and tetrahydropyran. Generally, the amount of diluent employed ranges from 1 to 50 mols per mol of sulfur dihalide.

The reaction is suitable conducted at a temperature of 0° C to the boiling point of the diluent, although temperatures between 0° C and 100° C are preferred. Generally, however, the conversion of the dithiazole hydrochloride salt (V) to the product (I) requires elevated temperatures, e.g., about 30° C to 100° C. The reaction is conducted at or above atmosphere pressure. The reaction time will, of course, vary depending on the reaction temperature and the particular reactants employed. Generally, however, the reaction time varies from one-half hour to 24 hours. The progress of the reaction can sometimes be determined by the evolution of hydrogen halide gas from the reaction mixture and the completion of the reaction can sometimes be determined by the cessation of gas evolution.

The chlorodisulfide intermediate (IV) and the dithiazole hydrohalide salt (V) formed in the reaction (1) are generally not isolated and are converted directly to the dithiazole (I) during the course of the reaction.

The N-aryl cyanothioformamide reactant (II) is a known compound, and is generally prepared by the reaction of an aryl isothiocyanate and a metal cyanide, as disclosed in U.S. Pat. No. 3,287,102, issued Nov. 22, 1966 to J. F. Olin.

EXAMPLE 1

Preparation of 4-chloro-5-phenylimino-1,2,3-dithiazole

A solution of 13.5 g (0.1 mol) phenyl isothiocyanate and 6.5 g (0.1 mol) potassium cyanide in 100 ml ethanol and 40 ml water was stirred at about 25° C for 1 hour. The solution was then diluted with water, slurried with charcoal and filtered. The filtrate was acidified with concentrated hydrochloric acid. An oil was separated on acidification. The oil solidified on standing and the resulting solid was filtered. The solid was then recrystallized from benzene/hexane to give 12.8 g N-phenyl cyanothioformamide, as a orange solid melting at 73°-81° C.

A solution of 10.0 g N-phenyl cyanothioformamide in 50 ml dimethoxyethane was added dropwise over a period of 40 minutes to an ice-bath cooled solution of 7 g sulfur dichloride in 200 ml dimethoxyethane. Ten drops of dimethylformamide and 0.5 g of tetraethylammonium chloride were added to the resulting solution. The reaction mixture was then stirred for 24 hours. A solid separated from the reaction mixture. The solid was filtered and heated in 25 ml benzene until gas evolution ceased and a homogeneous solution was obtained. The benzene was then evaporated to give an oil. The oil was crystallized from hexane to give 10 g of 4-chloro-5-phenylimino-1,2,3-dithiazole, as a bright yellow solid melting at 63°-65° C. The compound and its elemental analysis are tabulated in Table I as compound No. 1.

EXAMPLE 2

Preparation of 4-chloro-5-(2-methyl-4-chlorophenylimino)-1,2,3-dithiazole

A 50 ml sample of water was added slowly to 18 g 2-methyl-4-chlorophenyl isothiocyanate and 7 g potassium cyanide in 150 ml ethanol. The resulting dark red solution was stirred at about 25° C for 18 hours. The reaction mixture was then diluted with about 800 ml water, decolorized with charcoal and acidified with concentrated hydrochloric acid. A solid separated. The solid was filtered, taken up in benzene, decanted from a little water, treated with charcoal and diluted with hexane. On cooling, 9.8 g of N-(2-methyl-4-chlorophenyl) cyanothioformamide crystallized as an orange solid, m.p. 105°-106° C.

A solution of 4 g sulfur dichloride in 25 ml dichloromethane was added dropwise over 55 minutes to a solution of 7.5 g N-2-methyl-4-chlorophenyl cyanothioformamide and 1 g tetraethylammonium chloride in 50 ml dichloromethane. Gas was evolved from the reaction solution. The reaction solution was stirred at ambient temperature (about 25° C) for 18 hours during which time a solid separated (5.3 g). Recrystallization of the solid from benzene/hexane gave 4-chloro-5-(2-methyl-4-chlorophenylimino)-1,2,3-dithiazole as yellow crystals, m.p. 130°-131° C. The product and its elemental analysis are tabulated in Table I as compound No. 2.

EXAMPLE 3

Preparation of 4-chloro-5-(3-4-dichloro phenylimino)-1,2,3-dithiazole

A 13 g sample of N-(3,4-dichlorophenyl) cyanothioformamide in 50 ml dimethoxyethane was added dropwise over 40 minutes to a cooled (ice bath) solution of 7.4 g sulfur dichloride in 50 ml dimethoxyethane. The ice bath was removed and 0.5 g of dimethylformamide was added to the reaction mixture. The reaction was then stirred at about 25° C for 3 hours, during which time a yellow solid separated. The yellow solid was filtered and heated under reflux in 50 ml toluene for 10 minutes during which time gas was evolved and the reaction mixture became homogenous. The toluene was then evaporated under reduced pressure to give a solid residue. The residue recrystallized from hexane/benzene to give 11. g of product, as a yellow solid, m.p. 89°-90° C. The product and its elemental analysis are tabulated in Table I as compound No. 5.

Other compounds of the invention were prepared by procedures similar to those of Examples 1-3. These compounds are reported in Table I.

FUNGICIDAL UTILITY

The compounds of the invention are useful for controlling fungi, particularly plant fungal infections caused by *Botrytis cinerea*, leaf blights caused by organisms such as *Pythrium ultimum, Helminthosporum sativum, Fusarium moniliforme, Rhizoctonia solani, Monolinia fructicola* and *Uromyces phaseoli typica*. However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5-80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLE 4

Tomato Late Blight

Compounds of the invention were tested for the control of the Tomato Late Blight organism *Phytophthora infestans conidia.* Five- to six-week-old tomato (variety Bonny Best) seedlings were used. The tomato plants were sprayed with a 250-ppm solution of the test compound in acetone, water and a small amount of a nonionic emulsifier. The sprayed plants were then inoculated one day later with the organism, placed in an environmental chamber and incubated at 66°–68° F and 100% relative humidity for at least 16 hours. Following the incubation, the plants were allowed to dry and then were maintained at 60–80% relative humidity for approximately 7 days. The percent disease control provided by a given test compound was based on the percent disease reduction relative to untreated check plants. The compounds giving effective control at the test concentration are tabulated in Table II.

EXAMPLE 5

Tomato Early Blight

Compounds of the invention were tested for the control of the Tomato Early Blight organism, *Alternaria solani conidia.* Tomato (variety Bonny Best) seedlings of 6 to 7 weeks old were used. The tomato plants were sprayed with a 250-ppm solution of the test compound in an acetone-and-water solution containing a small amount of a non-ionic emulsifier. The sprayed plants were inoculated one day later with the organism, dried and maintained at 60–80% relative humidity for about 12 days. Percent disease control was based on the percent disease development on untreated check plants. The compounds giving effective control at the test concentration are tabulated in Table III.

EXAMPLE 6

Celery Late Blight

Compounds of the invention were tested for the control of Celery Late Blight using celery (Utah) plants 11 weeks old. The Celery Late Blight organism was *septoria apii.* The Celery plants were sprayed with solutions of the candidate toxicant mixed with acetone, water and a nonionic emulsifier. The plants were then inoculated with the organism and placed in an environmental chamber and incubated at 66°–68° F in 100% relative humidity for an extended period of time (approximately 48 hours). Following the incubation, the plants were allowed to dry and then were maintained at a 60–80% relative humidity for approximately 14 days. The percent disease control provided by a given candidate toxicant is based on the percent disease reduction relative to untreated check plants. The compounds giving effective control at the test concentrations are reported in Table IV.

EXAMPLE 7

*Botrytis cinerea* control 4-chloro-5-(2-methyl-4-chlorophenylimino)-1,2,3-dithiazole was tested for *Botrytis cinerea* control using detached, well-developed primary leaves of a 4–6 week old horsebean plant. The leaves were dipped into a 40-ppm solution of the test compound in acetone and water containing a small amount of a nonionic emulsifier, then taken out and placed in a petri plate lined with two pieces of filter paper. The leaves were allowed to dry while the filter paper was kept moist by adding water as required. The treated leaves were then inoculated with the spores of *Botrytis cinerea* fungus grown on potato dextrose agar. The plate was covered after inoculation and kept at 23.5° C. The filter-paper lining of the plate was kept saturated with water throughout the test. The rate of disease incidence was determined in 3 to 5 days, when the disease symptoms were fully evident on non-treated check leaves. The percentage disease control provided by the test compound was calculated as the percentage disease reduction based on the non-treated check leaves. The test compound was found to give 92% control.

EXAMPLE 8

Powdery Mildew

The powdery mildew test was made using bean seedlings (var. Bountiful) with well-developed primary leaves. The pathogen was *Erysiphe polygoni*. The bean seedlings were sprayed with a 250-ppm solution of the test compound in an acetone-water mixture containing a nonionic emulsifier. The treated plants were inoculated one day after spray application of the test compound with the pathogen. The plants were then maintained in a greenhouse at a 60–80% relative humidity and at a temperature of 68°–70° F. The rate of infection on the leaves was made after about 10 days. The percent disease control provided by a given test compound was based on the disease reduction relative to untreated check plants. The compounds of the invention giving effective control at the test concentrations are reported in Table V.

EXAMPLE 9

Mycelia Inhibition

The compounds of the present invention were evaluated for fungicidal effectiveness by means of a mycelial inhibition test. This test is designed to measure the fungitoxic activity of fungicidal chemicals in terms of their degree of inhibition of mycleium growth. Each compound to be tested was dissolved in acetone to 500 ppm concentration. Paper strips were innoculated with the particular mycelium growth by covering the paper with a potato dextrose broth culture of mycelial suspension. The innoculated papers were then placed on potato dextrose agar plates and sprayed by means of a micro sprayer with the fungicidal solution. The treated paper strips were incubated at 25° C and data is taken after 24 hours. Fungicidal activities are measured by a zone of inhibited mycelial growth from the center of the paper strip. The effectiveness of the compounds tested for fungicidal activity is reported in Table VI in terms of the microgram/cm$^2$ for 99% control of the fungus.

HERBICIDAL UTILITY

The compounds of the present invention are also herbicidal in post-emergent applications. For post-emergent applications, the herbicidal compounds will generally be applied directly to the foliage and other plant parts. Generally, the herbicidal compounds of the invention are effective against weed grasses as well as broadleaved weeds. Some may be selective with respect to the type of application and/or type of weed.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust, powder or granules. In the herbicidal composition, the active herbicidal compounds can be from about 0.01 to 95% by weight of the entire composition.

Suitable liquid diluent carriers such as benzene, toluene, kerosene, diesel oil, fuel oil, and petroleum naphtha. Suitable solid carriers are natural clays such as kaolinite, atapulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known at wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally for both pre- and post-emergent control, the herbicidal compounds of the invention are applied at rates of 0.2 to 60 kg/ha, and the preferred rate is in the range 0.5 to 40 kg/ha.

EXAMPLE 10

Herbicidal Tests

Post-emergent herbicidal tests with representative compounds of this invention were made using the following method.

An acetone solution of the test compound was prepared by mixing 750 mg of the compound, 220 mg of a nonionic surfactant and 25 ml of acetone. This solution was added to approximately 125 ml of water containing 156 mg of surfactant.

This test solution was uniformly sprayed on 2 similar pots of 24-day-old plants (approximately 15 to 25 plants per pot) at a dose of 33 mcg/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table VII.

EXAMPLE 11

Mite Control Tests

Compounds of the invention were tested for the control mites and mite eggs by the following procedure.

Pinto bean leaves were invested with two spotted-mites (*Tetramuchus urticae*). The mites were then allowed to lay eggs on the leaves. After 48 hours, the leaves were dipped into a water/acetone solution containing a small amount of a non-ionic surfactant and 40-ppm of the test compound. The treated leaves were then maintained at 85° F. One day after treatment, the mortality of adult mites was determined, and seven days after treatment, the egg mortality (non-hatching eggs) was determined.

The results for the compounds found to have mite and mite egg control activity are tabulated in Table VIII.

TABLE IV-continued

| Compound No. | Celery Late Blight, % Control |
|---|---|
| 18 | 64 |
| 19 | 62 |
| 20 | 62 |
| 22 | 80 |
| 23 | 63 |
| 29 | 44 |
| 30 | 80 |

TABLE 1

Compounds of the Formula:

$$AR-N=C\underset{S}{\overset{S}{\diagup}}\overset{N}{\underset{\parallel}{\diagdown}}C-Cl$$

| Compound No. | Ar | Color | Melting Point, °C | Sulfur Calc. | Sulfur Found | Chlorine Calc. | Chlorine Found |
|---|---|---|---|---|---|---|---|
| 1 | φ | yellow | 63–65 | 28.0 | 27.1 | 15.5 | 16.5 |
| 2 | 4-Cl-φ | yellow | 108–109 | 24.4 | 24.7 | 27.0 | 26.0 |
| 3 | 3,5-Cl$_2$-φ | yellow | 112–114 | 21.6 | 21.4 | 35.7 | 35.7 |
| 4 | 2-CH$_3$-4-CL-φ | yellow | 130–134 | 23.1 | 23.0 | 25.6 | 25.4 |
| 5 | 3,4-Cl$_2$-φ | yellow | 89–90 | 21.6 | 20.9 | 35.7 | 35.2 |
| 6 | 2,4-Cl$_2$-φ | yellow | 91–92 | 21.6 | 21.2 | 35.7 | 34.9 |
| 7 | 2-CH$_3$-φ | orange | 92–93 | 26.4 | 29.4 | 14.6 | 14.5 |
| 8 | 3-NO$_2$-φ | yellow | 123–124 | 13.0 | 12.2 | 23.4 | 19.5 |
| 9 | 2-CH$_3$-4-Br$_2$-φ | yellow | 120–122 | 19.9 | 18.6 | 6.2 | 6.7 |
| 10 | 2,6-(CH$_3$)$_2$-φ | yellow | 119–120 | 25.0 | 23.3 | 13.8 | 15.9 |
| 11 | 2,4,6-(CH$_3$)$_3$-φ | yellow | 99–100 | 23.7 | 22.7 | 13.1 | 15.1 |
| 12 | 3-Br-φ | yellow | 54–55 | 20.9 | 19.7 | 6.5 | 7.0 |
| 13 | 2,4-(CH$_3$)$_2$-φ | yellow | 92–93 | 25.0 | 24.6 | 13.8 | 13.7 |
| 14 | 2-Cl-φ | orange | 75–76 | 24.4 | 23.1 | 27.0 | 28.1 |
| 15 | 3-Cl-φ | yellow | 56–57 | 24.4 | 23.4 | 27.0 | 26.2 |
| 16 | 2-naphthyl | orange | 99–100 | 23.01 | 22.7 | 12.7 | 13.0 |
| 17 | 3-(2-CF$_3$-4-NO$_2$-φO)φ | yellow | 108–109 | 14.8 | 14.7 | 8.2 | 8.2 |
| 18 | 3-(4-NO$_2$-phenoxy)-φ | yellow | 122–123 | 17.5 | 17.9 | 9.7 | 9.9 |
| 19 | 4-(4-NO$_2$-phenoxy)-φ | yellow | 133–134 | 17.5 | 17.0 | 9.7 | 10.4 |
| 20 | 2-(4-NO$_2$-phenoxy)-φ | yellow | 108–109 | 17.5 | 18.3 | 9.7 | 10.0 |
| 21 | 2-CH$_3$-3-Cl-φ | yellow | 116–117 | 23.1 | 24.1 | 25.6 | 23.9 |
| 22 | 2-F-φ | yellow | 73–74 | 26.0 | 28.9 | 14.4 | 13.5 |
| 23 | 4-CN-φ | yellow | 149–151 | 25.3 | 25.8 | 16.0 | 15.3 |
| 24 | 4-F-φ | orange | 54–55 | 26.0 | 26.5 | 14.4 | 14.5 |
| 25 | 4-CH$_3$-φ | orange | 66–67 | 26.4 | 26.6 | 14.6 | 15.2 |
| 26 | 3,5-Cl$_2$-4-OH-φ | yellow | 132–134 | 20.5 | 20.7 | 33.9 | 32.9 |
| 27 | 4-benzoyl-φ | orange | 134–135 | 10.7 | 12.2 | 19.3 | 19.5 |
| 28 | 2-CH$_3$-5-Cl-φ | yellow | 111–112 | 23.1 | 23.2 | 25.6 | 24.5 |
| 29 | 2-CN-φ | orange | 131–133 | 25.3 | 25.8 | 14.0 | 13.4 |
| 30 | 3-(2-CN-4-CF$_3$-φO)φ | orange | — | 15.5 | 15.7 | 8.6 | 8.6 |

TABLE II

| Compound No. | Tomato Late Blight, % Control |
|---|---|
| 8 | 44 |
| 13 | 63 |
| 15 | 68 |
| 16 | 73 |
| 17 | 62 |
| 19 | 51 |
| 20 | 80 |
| 21 | 63 |
| 23 | 97 |

TABLE III

| Compound No. | Tomato Early Blight, % Control |
|---|---|
| 6 | 56 |
| 13 | 44 |
| 18 | 44 |
| 21 | 44 |
| 22 | 50 |
| 23 | 90 |

TABLE IV

| Compound No. | Celery Late Blight, % Control |
|---|---|
| 17 | 56 |

TABLE V

| Compound No. | Powdery Mildew % Control |
|---|---|
| 3 | 76 |
| 4 | 100 |
| 9 | 99 |
| 21 | 100 |
| 28 | 90 |

TABLE VI

| Compound No. | Mycelia Inhibition, micrograms/cm$^2$ for 99% control | | | | |
|---|---|---|---|---|---|
| | P | R | A | F | B |
| 1 | >1.7 | >1.7 | >1.7 | >1.7 | 0.33 |
| 2 | 0.39 | 0.33 | 0.85 | 1.5 | — |
| 3 | >1.7 | 0.98 | >1.7 | >1.7 | — |
| 4 | >1.7 | 0.63 | >1.7 | >1.7 | — |
| 5 | >1.7 | >1.7 | 1.1 | >1.7 | — |
| 7 | >1.7 | >1.7 | 0.98 | >1.7 | >1.7 |
| 8 | >1.7 | >1.7 | >1.7 | >1.7 | 1.3 |
| 11 | >1.7 | 0.98 | >1.7 | >1.7 | >1.7 |
| 12 | >1.7 | 1.4 | >1.7 | >1.7 | >1.7 |
| 13 | >1.7 | >1.7 | 1.1 | >1.7 | >1.7 |
| 15 | >1.7 | 0.98 | >1.7 | >1.7 | >1.7 |
| 18 | >1.7 | 0.45 | >1.7 | >1.7 | >1.7 |
| 19 | >1.7 | 0.88 | >1.7 | >1.7 | — |
| 20 | >1.7 | 1.3 | >1.7 | >1.7 | — |
| 21 | >1.7 | 1.1 | >1.7 | >1.7 | 1.3 |
| 22 | 1.4 | 0.73 | 1.4 | 1.3 | — |
| 23 | >1.7 | 0.6 | >1.7 | 1.4 | 0.78 |

TABLE VI-continued

| Mycelia Inhibition, micrograms/cm² for 99% control | | | | | |
|---|---|---|---|---|---|
| Compound No. | P | R | A | F | B |
| 25 | — | 0.92 | 1.5 | >1.7 | 0.76 |
| 26 | >1.7 | 1.3 | >1.7 | >1.7 | >1.7 |

P = *Pythium ultimum*
R = *Rhizoctonia solani*
A = *Aspergillus niger*
F = *Fusarium moniloforma*
B = *Botrytis cinerea*

TABLE VII

| | Herbicidal Effectiveness | | | | |
|---|---|---|---|---|---|
| Compound No. | O | W | C | M | P | L |
| 1 | 0 | 10 | 20 | 85 | 70 | 80 |
| 2 | 15 | 85 | 20 | 100 | 95 | 95 |
| 3 | 35 | 85 | 55 | 100 | 100 | 100 |
| 4 | 20 | 30 | 20 | 70 | 85 | 70 |
| 5 | 35 | 55 | 30 | 100 | 100 | 100 |
| 6 | 30 | 55 | 35 | 100 | 95 | 100 |
| 7 | 0 | 0 | 0 | 70 | 70 | 60 |
| 8 | 0 | 0 | 0 | 30 | 40 | 35 |
| 9 | 0 | 0 | 0 | 30 | 30 | 25 |
| 10 | 0 | 0 | 0 | 60 | 30 | 75 |
| 12 | 30 | 30 | 30 | 85 | 55 | 100 |
| 13 | 0 | 0 | 0 | 35 | 35 | 50 |
| 14 | 0 | 40 | 30 | 93 | 100 | 100 |
| 15 | 30 | 45 | 10 | 85 | 80 | 98 |
| 16 | 0 | 90 | 20 | 85 | 70 | 100 |
| 21 | 0 | 15 | 0 | 50 | 20 | 45 |
| 22 | 0 | 20 | 0 | 70 | 70 | 85 |
| 24 | 40 | 60 | 60 | 70 | 70 | 100 |
| 25 | 30 | 55 | 35 | 90 | 45 | 100 |
| 28 | 45 | 65 | 20 | 100 | 95 | 100 |

O = Wild Oats (*Avena fatua*)
W = Watergrass (*Echinochloa crusgalli*)
C = Crabgrass (*Digitaria sanguinalis*)
L = Mustard (*Brassica arvensis*)
M = Pigweed (*Amaranthus retroflexus*)
P = Lambsquarter (*Chenopodium album*)

TABLE VIII

| Compound No. | Mite Control, % | Mite Eggs Control, % |
|---|---|---|
| 3 | 90 | 85 |
| 4 | 94 | 100 |
| 5 | 99 | 100 |
| 6 | 100 | 0 |
| 9 | 70 | 100 |
| 12 | — | 78 |
| 13 | 0 | 30 |
| 14 | 70 | 0 |
| 19 | 0 | 78 |
| 21 | 90 | 99 |
| 22 | 0 | 39 |
| 28 | 85 | 85 |

What is claimed is:
1. A compound of the formula

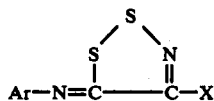

wherein X is fluoro, chloro, bromo, iodo and Ar is phenyl, naphthyl or phenyl or naphthyl substituted with 1 to 3 of the same or different substituents selected from hydroxy, fluoro, chloro, bromo, iodo, cyano, nitro, benzoyl, formyl, alkanoyl of 2 to 6 carbon atoms, alkyl of 1 to 6 carbon atoms, haloalkyl of 1 to 2 carbon atoms and 1 to 5 of the same or different halogens selected from fluoro, chloro or bromo, alkoxy of 1 to 4 carbon atoms, phenoxy, or phenoxy substituted with 1 to 2 of the same of different substituents selected from fluoro, chloro, bromo, iodo, trifluoromethyl, trichloromethyl, nitro, cyano or alkyl of 1 to 4 carbon atoms.

2. The compound of claim 1 wherein X is chloro or bromo.

3. The compound of claim 1 wherein X is chloro or bromo and Ar is phenyl, naphthyl or phenyl substituted with 1 to 2 of the same or different substituents selected from fluoro, chloro, bromo, iodo, cyano, nitro, benzoyl, alkyl of 1 to 4 carbon atoms, trifluoromethyl, trichloromethyl, phenoxy or phenoxy substituted with 1 to 2 of the same or different substituents selected from fluoro, chloro, bromo, iodo, nitro, trifluoromethyl, trichloromethyl, or alkyl of 1 to 4 carbon atoms.

4. The compound of claim 1 wherein X is chloro and Ar is phenyl, naphthyl or phenyl substituted with 1 to 2 of the same or different substituents selected from fluoro, chloro, bromo, iodo, or alkyl of 1 to 4 carbon atoms.

5. The compound of claim 1 wherein X is chloro and Ar is 2-methyl-4-chlorophenyl.

6. A process for preparing a compound of the formula

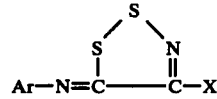

wherein Ar and X are as defined in claim 1 which comprises reacting substantially equimolar amounts of a sulfur dihalide wherein the halide is chloro or bromo and a N-aryl cyanothioformamide of the formula

wherein Ar is as defined above, in the liquid phase at a temperature of 0° to 100° C in the presence of a catalytic amount of an N,N-dialkylformamide or an N-alkylformamide wherein the alkyl groups have 1 to 4 carbon atoms, or a quaternary ammonium salt.

7. The process of claim 6 wherein the sulfur dihalide is sulfur dichloride.

8. The process of claim 7 wherein the N,N-dialkylformamide is N,N-dimethylformamide.

9. The process of claim 7 wherein the quaternary ammonium salt is a lower-tetraalkylammonium halide salt.

* * * * *